(12) United States Patent
Ryu

(10) Patent No.: US 8,471,082 B2
(45) Date of Patent: Jun. 25, 2013

(54) PROCESS FOR CONVERTING METHANE TO ETHYLENE

(75) Inventor: J. Yong Ryu, Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 1472 days.

(21) Appl. No.: 12/049,114

(22) Filed: Mar. 14, 2008

(65) Prior Publication Data

US 2009/0234167 A1 Sep. 17, 2009

(51) Int. Cl.
*C07C 5/09* (2006.01)

(52) U.S. Cl.
USPC ........... 585/263; 585/250; 585/258; 585/259; 585/271; 585/324; 585/943

(58) Field of Classification Search
USPC .................. 585/271, 250, 258, 259, 263, 943, 585/324
See application file for complete search history.

(56) References Cited

U.S. PATENT DOCUMENTS

| | | | |
|---|---|---|---|
| 3,725,495 A * | 4/1973 | Wrisberg et al. ............. | 585/414 |
| 4,128,595 A * | 12/1978 | Montgomery ................ | 585/261 |
| 4,302,356 A | 11/1981 | Smith, Jr. | |
| 4,443,559 A | 4/1984 | Smith, Jr. | |
| 4,731,229 A | 3/1988 | Sperandio | |
| 4,981,829 A * | 1/1991 | Shutt et al. ..................... | 502/202 |
| 5,073,236 A | 12/1991 | Gelbein et al. | |
| 5,266,546 A | 11/1993 | Hearn | |
| 5,431,890 A | 7/1995 | Crossland et al. | |
| 5,730,843 A | 3/1998 | Groten et al. | |
| 5,811,621 A | 9/1998 | van Dijk | |
| 5,840,259 A | 11/1998 | Adams | |
| 6,040,489 A * | 3/2000 | Imai .............................. | 585/260 |
| 6,169,218 B1 * | 1/2001 | Hearn et al. .................. | 585/260 |
| 6,212,905 B1 | 4/2001 | Kuechler et al. | |
| 6,495,732 B1 * | 12/2002 | Hearn et al. ................... | 585/664 |
| 6,509,292 B1 * | 1/2003 | Blankenship et al. ........ | 502/330 |
| 6,717,022 B2 * | 4/2004 | Ryu et al. ...................... | 585/261 |
| 6,734,328 B1 * | 5/2004 | Ryu .............................. | 585/275 |
| 6,774,275 B2 | 8/2004 | Smith, Jr. et al. | |
| 7,014,750 B2 | 3/2006 | Boger et al. | |
| 7,045,670 B2 | 5/2006 | Johnson et al. | |
| 7,208,647 B2 * | 4/2007 | Peterson et al. ............. | 585/324 |
| 7,288,686 B2 * | 10/2007 | Ryu .............................. | 585/259 |
| 2005/0090701 A1 * | 4/2005 | Gelbein et al. ................ | 585/259 |

(Continued)

OTHER PUBLICATIONS

Arutyunov, V.S. et al., Pyrolysis of Methane in the Temperature Range 100-1700 K, Russian Chemical Review (1991), pp. 1384-1397.*

(Continued)

*Primary Examiner* — In Suk Bullock
*Assistant Examiner* — Bradley Etherton
(74) *Attorney, Agent, or Firm* — Osha • Liang LLP

(57) ABSTRACT

A process for the production of ethylene, the process including: feeding hydrogen, a heavy solvent, a light solvent, and acetylene to a down-flow reactor comprising at least one reaction zone comprising a hydrogenation catalyst; concurrently in the down-flow reactor: contacting acetylene and hydrogen in the presence of the hydrogenation catalyst to convert at least a portion of the acetylene to ethylene; boiling at least a portion of the light solvent from a liquid phase to a vapor phase; recovering a reactor effluent comprising heavy solvent, light solvent, and ethylene; condensing at least a portion of the light solvent in the vapor phase; recovering a solvent fraction comprising the heavy solvent and the light solvent; recovering a product fraction comprising ethylene.

20 Claims, 2 Drawing Sheets

U.S. PATENT DOCUMENTS

| | | | |
|---|---|---|---|
| 2005/0256353 A1* | 11/2005 | Boyer | 585/259 |
| 2006/0155154 A1* | 7/2006 | Ryu et al. | 585/259 |
| 2006/0173224 A1* | 8/2006 | Putman et al. | 585/258 |
| 2006/0229477 A1* | 10/2006 | Smith et al. | 585/259 |
| 2007/0149835 A1* | 6/2007 | Cheung et al. | 585/258 |
| 2009/0326288 A1 | 12/2009 | Mamadov et al. | |

OTHER PUBLICATIONS

Lide, CRC Handbook of Chemistry and Physics, D. R. Lide, ed., 91st ed., 2011 Internet version—2011, month unknown.*

* cited by examiner

PROCESS FOR CONVERTING METHANE TO ETHYLENE

BACKGROUND OF DISCLOSURE

1. Field of the Disclosure

Embodiments disclosed herein relate generally to the conversion of hydrocarbons or hydrocarbon-containing mixtures to ethylene. In another aspect, embodiments disclosed herein relate to the conversion of methane to ethylene. In another aspect, embodiments disclosed herein relate to the selective hydrogenation of acetylene to ethylene.

2. Background

Natural gas typically contains about 60 to 100 mole percent methane, the balance being primarily heavier alkanes. Alkanes of increasing carbon number are normally present in decreasing amounts. Carbon dioxide, hydrogen sulfide, nitrogen, and other gases may also be present in relatively low concentrations.

The economical conversion of methane into valuable reactive hydrocarbon and reactive non-hydrocarbon products has been a technological goal for many years. For example, light olefins, such as ethylene and propylene, serve as the building blocks for the production of numerous chemicals. For example, intermediate and end uses of ethylene include production of plastics, resins and fibers, and a host of other products.

Methane may be converted to ethylene via methanol or dimethyl ether. Methane may be first converted to syngas, which is subsequently converted to methanol or a mixture of dimethyl ether and methanol. The methanol and/or dimethyl ether may then be converted to ethylene in a final step. Production of ethylene from methane via methanol is disclosed in, for example, U.S. Pat. No. 5,811,621.

Methane may also be converted to a mixture of unsaturated hydrocarbons and hydrogen by partial oxidation or non-oxidative pyrolysis, as described at length in U.S. Pat. No. 7,208,647. Such conversion processes may result in a product stream including hydrogen, carbon monoxide, carbon dioxide, water, methane, acetylene, ethylene, and other hydrocarbons. Similar feedstocks may also be produced by cracking or partial oxidation of various hydrocarbon feeds, such as ethane, propane, and other saturated hydrocarbons. U.S. Pat. No. 6,212,905 describes various processes converting methane to ethylene via cracking.

As noted above, acetylene is a by-product for various processes converting methane to ethylene. Acetylene, the simplest alkyne, may be converted to ethylene by hydrogenation. It is typically desirable to convert acetylene to ethylene, but not to convert ethylene to ethane by further hydrogenation, thus resulting in the valuable reactive olefin. The hydrogenation of acetylene to ethylene may be carried out on the raw pyrolysis gas mixture (front-end hydrogenation), or may be carried out following some separation of the various components (tail-end hydrogenation), such as where the only stream subject to hydrogenation is enriched in highly unsaturated compounds (e.g., acetylene).

The advantage of primary gas hydrogenation is generally an abundance of the hydrogen required for hydrogenation. The concentrations of acetylene and hydrogen in the pyrolysis gas mixture are quite high compared with ethane steam cracked products. The mole ratio of hydrogen to acetylene in a pyrolysis gas mixture is approximately 5 to 1. Unfortunately, the excess available hydrogen in front-end hydrogenation can result in "run-away" reactivity, resulting in conversion of alkenes to alkanes and reducing the value of the product. Fractionation reduces the available hydrogen, but polymer formation is common, the effect of which is to shorten the useful life of the catalyst.

As described in EP 01710222, acetylene in the pyrolysis product stream may be selectively hydrogenated to ethylene in the presence of a catalyst in a fixed bed reactor. Various other processes for the hydrogenation of acetylene are described in U.S. Pat. Nos. 7,045,670 and 7,014,750 and U.S. Patent Application Publication No. 20060155154, for example.

Various problems associated with selective hydrogenation of acetylene to ethylene include poor selectivity of ethylene and fast catalyst deactivation due to the formation of undesired "green oil." Such problems often make the conversion of methane to ethylene unattractive for commercial production of ethylene.

Accordingly, improvements in the selective hydrogenation of acetylene to ethylene are needed.

SUMMARY OF THE DISCLOSURE

In one aspect, embodiments disclosed herein relate to a process for the production of ethylene, the process including: feeding hydrogen, a heavy solvent, a light solvent, and acetylene to a down-flow reactor comprising at least one reaction zone comprising a hydrogenation catalyst; concurrently in the down-flow reactor: contacting acetylene and hydrogen in the presence of the hydrogenation catalyst to convert at least a portion of the acetylene to ethylene; boiling at least a portion of the light solvent from a liquid phase to a vapor phase; recovering a reactor effluent comprising heavy solvent, light solvent, and ethylene; condensing at least a portion of the light solvent in the vapor phase; recovering a solvent fraction comprising the heavy solvent and the light solvent; recovering a product fraction comprising ethylene.

In another aspect, embodiments disclosed herein relate to a process for the production of ethylene, the process including: feeding hydrogen, a heavy solvent, a light solvent, and acetylene to a catalytic distillation reactor system comprising at least one reaction zone comprising a hydrogenation catalyst; concurrently in the catalytic distillation reactor system: contacting acetylene and hydrogen in the presence of the hydrogenation catalyst to convert at least a portion of the acetylene to ethylene; fractionating the feed components to form a light fraction, comprising the light solvent and ethylene, and a heavy fraction, comprising the heavy solvent; recovering the light fraction from the catalytic distillation reactor system as a first overheads fraction; recovering the heavies fraction from the catalytic distillation reactor system as a first bottoms fraction; condensing at least a portion of the first overheads fraction to form a vapor fraction comprising ethylene and a liquid fraction comprising the light solvent; returning at least a portion of the liquid fraction to the catalytic distillation reactor system as a reflux; and returning at least a portion of the heavies fraction to the catalytic distillation reactor system at a location above the at least one reaction zone.

In another aspect, embodiments disclosed herein relate to a process for converting methane to ethylene, the process including: heating methane to a temperature of at least 1200° C. to form a pyrolysis composition comprising acetylene, ethylene, hydrogen, carbon monoxide, carbon dioxide, and methane; feeding a heavy solvent, a light solvent, and the pyrolysis composition to a catalytic distillation reactor system comprising at least one reaction zone comprising a hydrogenation catalyst; concurrently in the catalytic distillation reactor system: contacting acetylenes and hydrogen in the presence of the hydrogenation catalyst to convert at least a portion of the acetylenes to ethylene; fractionating the feed components to form a light fraction, comprising the light solvent, ethylene and components lighter than ethylene, and a heavy fraction, comprising the heavy solvent; recovering the light fraction from the catalytic distillation reactor system as a first overheads fraction; recovering the heavies fraction from the catalytic distillation reactor system as a first bottoms fraction; condensing at least a portion of the first overheads fraction to form a vapor fraction, comprising ethylene and components lighter than ethylene, and a liquid fraction, comprising the light solvent; returning at least a portion of the liquid fraction to the catalytic distillation reactor system as a reflux; and returning at least a portion of the heavies fraction to the catalytic distillation reactor system at a location above the at least one reaction zone.

Other aspects and advantages will be apparent from the following description and the appended claims.

DETAILED DESCRIPTION

Figure 1:
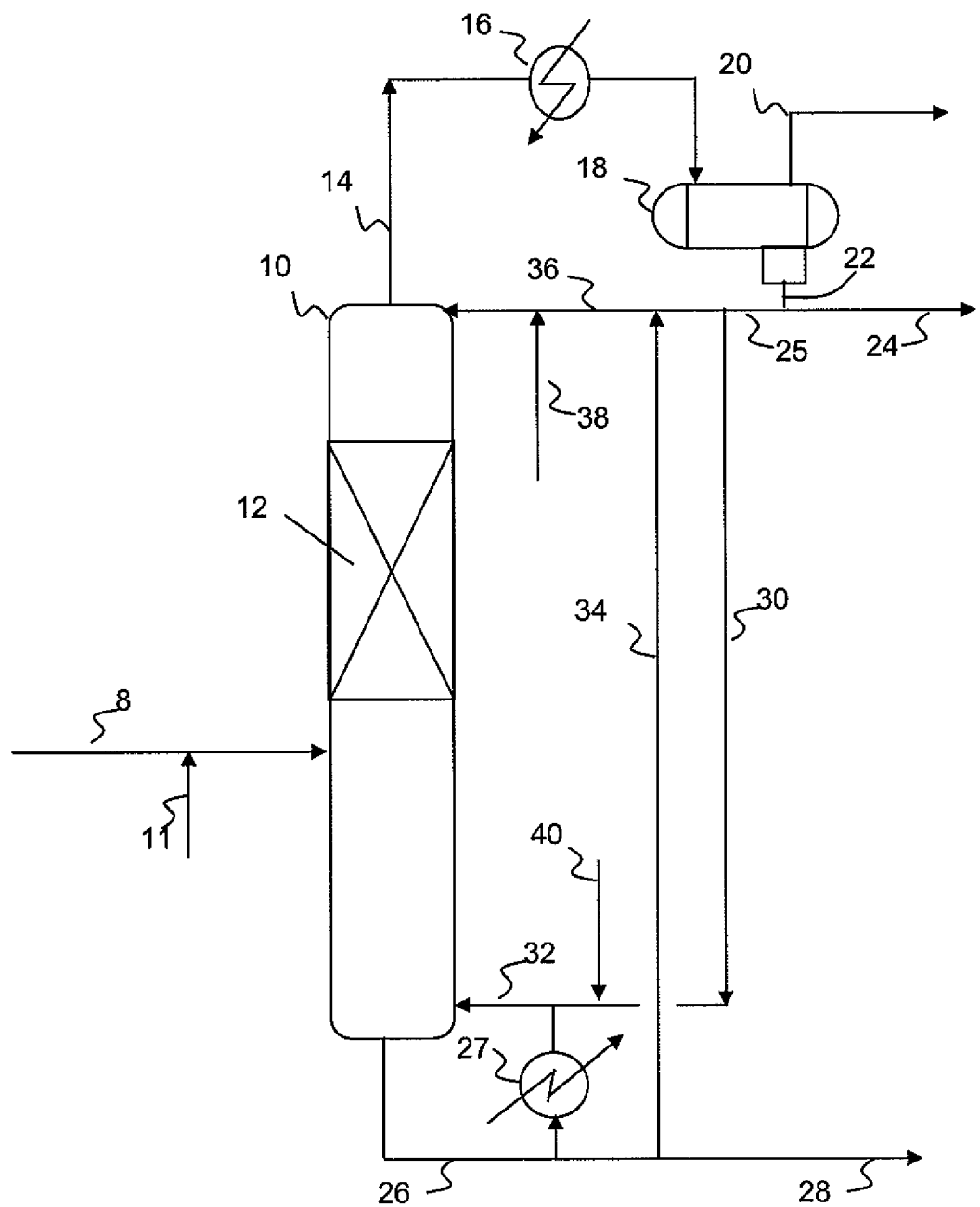
FIG. 1 is a simplified flow diagram of a process for the conversion of methane to ethylene according to embodiments disclosed herein.

In one aspect, embodiments disclosed herein relate to the conversion of hydrocarbons or hydrocarbon-containing mixtures to ethylene. In another aspect, embodiments disclosed herein relate to the conversion of methane to ethylene. In another aspect, embodiments disclosed herein relate to the selective hydrogenation of acetylene to ethylene. The conversion of hydrocarbon or hydrocarbon-containing mixtures to ethylene, according to embodiments disclosed herein, may be performed in two steps: 1) conversion of the hydrocarbon to a mixture containing acetylene, and 2) acetylene in the product stream may be selectively hydrogenated to ethylene in the presence of a hydrogenation catalyst and a solvent system, including a heavy solvent and a light solvent.

The source of acetylene may be from any process, such as pyrolysis, thermal cracking, steam cracking, partial oxidation, or other like process where hydrocarbons or hydrocarbon-containing streams are thermally and/or chemically modified to produce increased quantities of unsaturated compounds, such as acetylene, ethylene, and the like.

In certain embodiments, feed streams containing ethylene and acetylene may be obtained from the pyrolysis or partial oxidation of methane or natural gas. Pyrolysis of methane may occur, for example, at temperatures in excess of 1200° C. in other embodiments, such as for thermal cracking of methane or natural gas.

Pyrolysis of methane may occur, for example, at temperatures in excess of 500° C. in some embodiments, such as where the reaction is catalyzed Catalysts useful for the oxidative conversion of methane to ethylene may include zinc oxide, calcium oxide, silicon carbide, and others, such as disclosed in U.S. Pat. No. 4,981,829. In some embodiments, partial oxidation or pyrolysis of methane or natural gas may occur at temperatures in excess of 1200° C. in the presence of a catalyst, such as a noble metal catalyst.

The product resulting from the cracking or partial oxidation of hydrocarbon streams, such as methane and natural gas, may include a mixture of various compounds, including one or more of hydrogen, carbon monoxide, carbon dioxide, methane, water, acetylene, ethylene, and other hydrocarbons.

The selective hydrogenation of acetylene to ethylene performed in embodiments disclosed herein may be a front-end hydrogenation or a tail-end hydrogenation. Catalysts useful for the selective hydrogenation of acetylene to ethylene typically contain one or more metals selected from Group VIII of the Periodic Table, such as palladium, ruthenium, platinum, nickel, etc., or catalysts containing one or more noble metals, such as silver. In some embodiments, the Group VIII catalyst or mixture of Group VIII catalysts may be co-formulated with other metals, such as those from Groups I through VII, and may be support on silica, alumina, alumina-silica, and other various supports.

When used in a catalytic distillation reactor system, to facilitate fractionation and catalytic activity, the above described catalysts may be prepared in the form of a distillation structure. The catalytic distillation structure must be able to function as catalyst and as mass transfer medium. The catalyst must be suitably supported and spaced within the column to act as a catalytic distillation structure.

In some embodiments, the catalyst is contained in a structure as disclosed in U.S. Pat. No. 5,730,843, which is hereby incorporated by reference. In other embodiments, one or more of the above-described catalysts may be contained in a plurality of wire mesh tubes closed at either end and laid across a sheet of wire mesh fabric such as demister wire. The sheet and tubes are then rolled into a bale for loading into the distillation column reactor. This embodiment is described, for example, in U.S. Pat. No. 5,431,890, which is hereby incorporated by reference. Other useful catalytic distillation structures are disclosed in U.S. Pat. Nos. 4,302,356, 4,443,559, 4,731,229, 5,073,236, 5,431,890, 5,266,546, and 5,730,843, which are each incorporated by reference.

Carbon monoxide, which may enhance the hydrogenation selectivity to ethylene, may be present in the feed, such as for a front-end hydrogenation, or may be added to the feed, such as for a tail-end hydrogenation.

Since acetylene is a very reactive material, it is very easily polymerized in a selective hydrogenation reaction zone. Such polymerizations may cause low selectivity to the desired product, ethylene, and may cause rapid catalyst deactivation. Additionally, such as for front-end hydrogenation, the concentration of acetylene and hydrogen in the feed stream may cause uncontrollable temperature run-away reactions and poor ethylene selectivity.

These problems may be addressed by performing the selective hydrogenation in the presence of suitable solvent systems. Solvent systems useful in embodiments disclosed herein may include two or more components, including a high boiling component (heavy solvent) and a low boiling component (light solvent). As used herein, heavy solvents are typically non-volatile or have a low partial pressure at reaction conditions (temperature and pressure), whereas light solvents have a boiling point at or near the reaction conditions, exhibiting at least some degree of volatility when in the reaction zone at reaction conditions. The choice of light and heavy solvents should be appropriate for the reaction conditions as described below, where a solvent appropriate for operation at the low end of the range may not be suitable for operation at the high end of the range give.

The selective hydrogenations disclosed herein may be performed in the liquid phase in the presence of dual phase liquid and vapor, such as in a catalytic distillation reactor system, a boiling point reactor, a pulsed flow reactor, or a combination of these reactors. Pulsed flow reactors and boiling point reactors are described in, for example, U.S. Pat. Nos. 6,774,275 and 5,840,259 and U.S. Patent Application Publication No. 20060229477, each of which are incorporated herein by reference. These reactors may include one or more reactions zones containing a hydrogenation catalyst, as described above.

The selective hydrogenation may be carried out by contacting the acetylene and hydrogen in the presence of the hydrogenation catalyst at a temperature and for a time sufficient that molecular interactions effective to increase the saturation of the acetylene may occur, converting at least a portion of the acetylene to ethylene. Such reactions may be carried out at a temperature in the range from about 15° C. to about 205° C. (about 60° F. to about 400° F.) in some embodiments; and from about 20° C. to about 150° C. (about 70° F. to about 300° F.) in other embodiments. Pressures in the reaction zone may range from about 2.7 bar to about 16 bar (about 25 psig to about 220 psig) in some embodiments, and from about 4.5 bar to about 13.4 bar (about 50 psig to about 180 psig) in other embodiments.

The roles of the heavy solvents are maintaining a liquid phase in the catalytic reaction zone and washing off polymers or polymer precursors deposited on the catalyst surface, prolonging catalyst cycle length. Selection of high boiling components should be placed in improving selective absorption of acetylene into the liquid phase. The heavy solvent may have a greater affinity for acetylene than ethylene as defined by a Henry's constant ratio of acetylene to ethylene of less than unity ($K_{AC}/K_{ET}<1$ where $K_n=P_n/X_n$ and $P_n$ and $X_n$=partial pressure and mole fraction of a component n in liquid phase, respectively). In some embodiments, such solvents will have a higher Henry's constant ratio of acetylene to ethylene at a given condition than simple hydrocarbons, such as hexane $(K_{AC}/K_{ET})_{HBS}/(K_{AC}/K_{ET})_{hexane}>1$. For example, the Henry's constant ratio of acetylene to ethylene for the high boiling solvent to that for hexane may be greater than 1.1 in some embodiments; greater than 1.25 in other embodiments; greater than 1.5 in other embodiments; greater than 2 in other embodiments; and greater than 5 in yet other embodiments.

Heavy solvents may include one or more of benzene, cyclohexane, toluene, acetonitrile, propionitrile, methylcyclohexane, tetrahydrofuran, furfural, diethyl ether, methyl ethyl ether, ethylamine, methyl tetrahydrofuran, dimethylformamide, cyclic organic carbonate esters, dimethylactamide, N-methylpyrorolidone, and formylmorpholine, for example. High boiling solvents, such as acetonitrile, may improve ethylene selectivity, and acetonitrile may be used as a sole high boiling solvent or may be used in high boiling solvent mixtures in various embodiments disclosed herein.

The role of the light solvent is primarily for controlling temperature for the selective hydrogenation, maintaining the temperature of the catalytic reaction zone in a desired range for selective hydrogenation of acetylene. Boiling off of the low boiling solvents takes away the heat of the hydrogenation reaction, resulting in a more constant temperature in the reaction zone, helpful in controlling acetylene concentration and ethylene concentration in the liquid phase, as well as preventing run away reactions. Light solvents may include one or more of butane, isobutane, isopentane, pentane, and dimethyl ether, for example.

Referring now to FIG. 1, one process for the selective hydrogenation of acetylene to ethylene according to embodiments disclosed herein is illustrated. Acetylene may be fed to a catalytic distillation reactor system 10 via flow line 8. Where the acetylene feed stream contains sufficient hydrogen for the desired hydrogenation, such as for a front-end hydrogenation, additional hydrogen may not be necessary. Where the acetylene feed stream contains little or no hydrogen, such as for a tail-end hydrogenation, additional hydrogen may be introduced to catalytic distillation reactor system 10 via flow line 11.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Catalytic distillation reactor system 10 may include at least one reaction zone 12 containing a hydrogenation catalyst. In some embodiments, the hydrogenation catalyst may be formed as a distillation structure, as described above. Catalytic distillation reactor system 10 may also include traditional non-catalytic distillation structures (trays and/or packing) above and below reaction zone 12 for fractionating the components.

The acetylene and hydrogen, in some embodiments, may be fed to the catalytic distillation reactor system 10 at a location below reaction zone 12. Acetylene and hydrogen may then distill upward within catalytic distillation reaction system 10, contacting the hydrogenation catalyst in reaction zone 12 and converting at least a portion of the acetylene to ethylene.

To facilitate the hydrogenation of acetylene to ethylene, a light solvent and a heavy solvent may be circulated through catalytic distillation reactor system 10. The light solvent may distill upward with the acetylene and hydrogen, while the heavy solvent may distill downward within catalytic distillation reactor system 10. The boiling of the components, including the light solvent, within catalytic distillation reactor system 10 may effectively remove heat generated during the hydrogenation of acetylene to ethylene, thus providing for improved hydrogenation reaction temperature control, as compared to a typical liquid phase fixed bed reactor. Additionally, the liquids traversing through the column may wash any polymeric deposits from the catalyst, thereby improving catalyst service life.

The light solvent, ethylene, and any unreacted hydrogen and acetylene may be recovered from catalytic distillation reactor system 10 as an overheads fraction via flow line 14. The overheads fraction may then be cooled via heat exchanger 16, and the resulting vapor and liquid phases may be collected and separated in overhead drum 18.

The vapor phase, including ethylene and any unreacted hydrogen and acetylene, may be recovered via flow line 20. The liquid phase, including the light solvent, may be recovered via flow line 22. If necessary, a portion of the liquid fraction may be purged via flow line 24. The remaining portion of the liquid fraction may be returned to the column via flow line 25 as reflux.

The heavy solvent and any heavy by-products from the hydrogenation of acetylene, such as polymeric materials or "green oil," may be recovered from catalytic distillation reactor system as a bottoms fraction via flow line 26. A portion of the bottoms fraction may be used to control vapor traffic through the column via reboiler 27. A portion of the bottoms fraction may be purged from the system via flow line 28 to avoid accumulation of hydrogenation by-products within catalytic distillation reactor system 10.

In some embodiments, it may be desirable to feed a portion of the liquid phase recovered in the overhead system to a bottom portion of the catalytic distillation reactor system, below reaction zone 12. For example, a portion of the liquid phase may be fed via flow line 22, combined with reboiler effluent, and fed to catalytic distillation reactor system 10 via flow line 32.

To facilitate the washing of the catalyst, as well as to dissolve a portion of the acetylene in the liquid phase within the reaction zone 12, a portion of the bottoms fraction 26 may be fed to catalytic distillation reactor system 10 at a location above reaction zone 12, such that heavy solvent may traverse the column countercurrent to the flow of acetylene and hydrogen. For example, a portion of the bottoms fraction may be fed via flow line 34, combined with the liquid fraction in flow line 25, and fed to catalytic distillation reactor system 10 as reflux via flow line 36.

Other feed locations for the feed of heavy solvent and light solvent to a location above and below reaction zone 12, respectively, may also be used. To account for loss of heavy solvent and light solvent via purge lines 24 and 28, make-up heavy and light solvent may be fed to catalytic distillation reactor system 10, such as via one or both of flow lines 38 and 40.

As described above, acetylene feed stream 8 may be an acetylene feed, or may be an feed stream containing acetylene, such as a pyrolysis gas or other mixtures containing acetylene. In such instances, acetylene feed stream 8 may also include various components such as water, hydrogen, carbon monoxide, carbon dioxide, methane, ethylene, and other heavier hydrocarbons. Such components may be recovered via one or more of flow lines 20, 24, and 28. For example, hydrocarbons heavier than ethylene may be recovered via flow line 24. Carbon monoxide, hydrogen, methane, and other light components may be recovered via flow line 20.

Where flow line 20 contains multiple components, flow line 20 may be fed to a separation system (not shown) for separating the various components and to recover a fraction having an enriched ethylene concentration. For example, one or more distillation columns may be used to recover a fraction containing greater than 90 weight percent ethylene in some embodiments; greater than 95 weight percent ethylene in other embodiments; and greater than 99, 99.5, 99.8, or 99.9 weight percent ethylene in other embodiments.

Figure 2:
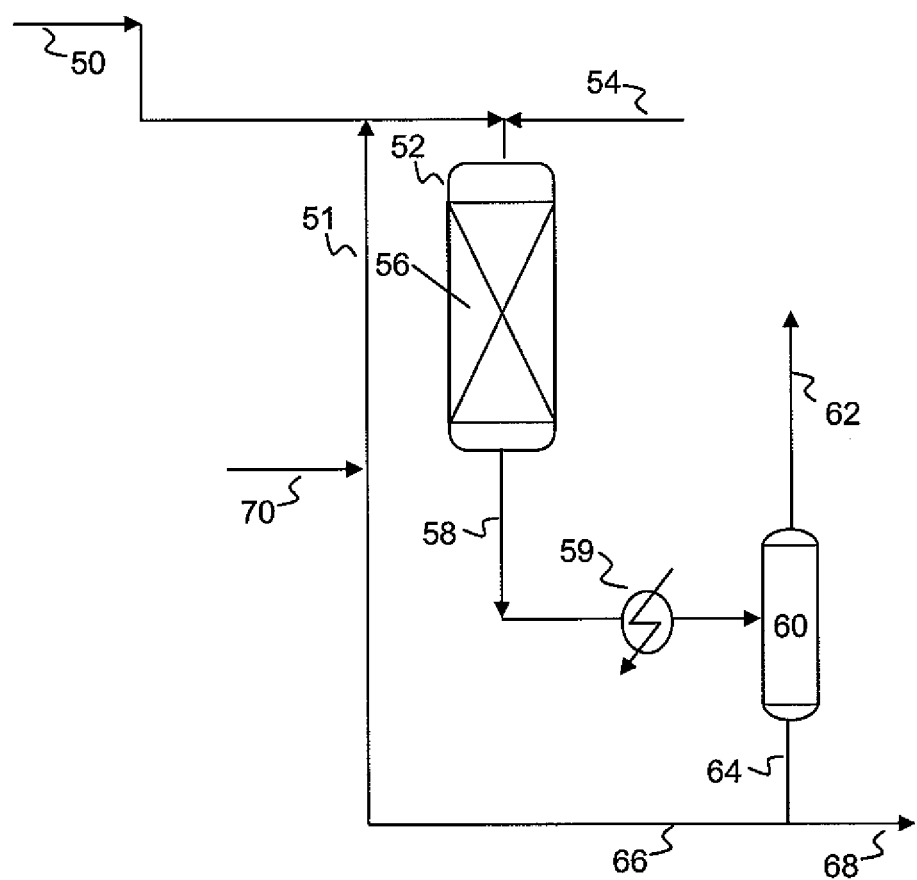
FIG. 2 is a simplified flow diagram of a process for the conversion of methane to ethylene according to embodiments disclosed herein.

Referring now to FIG. 2, acetylene feed stream 50 may be combined with a mixed solvent feed stream 51 and fed to a down-flow boiling point reactor 52. Where acetylene feed stream 50 contains insufficient hydrogen, additional hydrogen may be fed to reactor 52 via flow line 54. As above, acetylene feed stream 50 may be acetylene, or may include various other components, such as a raw pyrolysis gas or a fractionated pyrolysis gas for front-end hydrogenation or tail-end hydrogenation, respectively.

Down-flow boiling point reactor 52 may include at least one reaction zone 56 containing a hydrogenation catalyst. Contact of acetylene and hydrogen in the presence of the hydrogenation catalyst may convert at least a portion of the acetylene to ethylene. Mixed solvent feed stream 51 may include a mixture of a heavy solvent and a light solvent, where the heavy solvent may facilitate dissolution of acetylene in the liquid phase for contact with the hydrogenation catalyst. The heavy solvent may also wash the catalyst surface to remove any heavy by-products, such as polymers or "green oil." Conditions in the reaction zone 56 may be such that the light solvent is boiling, capturing at least a portion of the heat generated during the hydrogenation of acetylene, and helping to prevent run-away reactions that could cause hydrogenation of acetylene to ethane.

In some embodiments, the flow rate of the vapor traffic in reactor 52 may be such that reactor 52 is operated in the pulsed flow regime. Operation in the pulsed flow regime may farther aid in distribution and mixing of the various components throughout the reactor.

A reactor effluent, including the heavy solvent, light solvent, ethylene, and any unreacted hydrogen and acetylene may be recovered from reactor 52 via flow line 58. The reactor effluent may then be cooled via heat exchanger 59, condensing at least a portion of the light solvent in the vapor phase of the reactor effluent due to boiling conditions within reactor 52. The resulting vapor and liquid phases may be separated in splitter 60. A vapor fraction, including ethylene and any unreacted hydrogen and acetylene, may be recovered via flow line 62. Where flow line 62 contains multiple components, flow line 50 may be fed to a separation system (not shown) for separating the various and to recover a fraction having an enriched ethylene concentration.

A liquid fraction, including the light solvent, heavy solvent, and any heavy by-products from the hydrogenation of acetylene, may be recovered via flow line 64. At least a portion of the liquid fraction may be returned to the top of reactor 52 via flow line 66, and a portion may be purged via flow line 68, avoiding accumulation of by-products in the circulation loop. Make-up solvent fed via flow line 70, including light solvent and heavy solvent, may be combined with recycle solvent 66 and fed as solvent feed 51 to reactor 52. Solvent flow to the top of reactor 52, including recycle solvent and make-up solvent, should be sufficient to maintain the catalyst within reaction zone 56 as fully wetted.

Although illustrated in FIGS. 1 and 2 as a single reactor system, various combinations of catalytic distillation reactor systems, boiling point reactors, and pulsed flow reactors may be used, including reactors placed in parallel or reactors placed in series, where an effluent from a first reactor may be used as feed to a second reactor Additionally, such reactors may include one or more catalytic reaction zones.

As described above, embodiments disclosed herein provide for the selective hydrogenation of acetylene to ethylene. Advantageously, embodiments disclosed herein may improve the selectivity of the hydrogenation via use of a heavy solvent. Use of heavy solvents may also prolong catalyst cycle times. Additionally, use of light solvents in embodiments disclosed herein may prevent excessive temperatures, influencing both the reaction temperature control and the relative solubility of acetylene and ethylene in the liquid phase.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of ethylene, the process comprising:
   feeding hydrogen, a heavy solvent, a light solvent, and acetylene to a catalytic distillation reactor system comprising at least one reaction zone comprising a hydrogenation catalyst;
   concurrently in the catalytic distillation reactor system:
      contacting acetylene and hydrogen in the presence of the hydrogenation catalyst to convert at least a portion of the acetylene to ethylene;
      fractionating the feed components to form a light fraction, comprising the light solvent and ethylene, and a heavy fraction, comprising the heavy solvent;
   recovering the light fraction from the catalytic distillation reactor system as a first overheads fraction;
   recovering the heavy fraction from the catalytic distillation reactor system as a first bottoms fraction;
   condensing at least a portion of the first overheads fraction to form a vapor fraction comprising ethylene and a liquid fraction comprising the light solvent;
   returning at least a portion of the liquid fraction to the catalytic distillation reactor system as a reflux; and
   returning at least a portion of the heavy fraction to the catalytic distillation reactor system at a location above the at least one reaction zone,
   wherein the heavy solvent comprises at least one of cyclohexane, propionitrile, methylcyclohexane, furfural, ethylamine, dimethylformamide, cyclic organic carbonate esters, and dimethylacetamide.

2. The process of claim 1, wherein the hydrogen and acetylene are fed to the catalytic distillation reactor system at a location below the at least one reaction zone.

3. The process of claim 1, further comprising returning at least a portion of the liquid fraction to the catalytic distillation reactor system at a location below the at least one reaction zone.

4. The process of claim 1, further comprising:
   pyrolyzing methane to form a composition comprising carbon monoxide, carbon dioxide, methane, hydrogen, acetylene, ethylene, and heavier hydrocarbons;
   feeding at least a portion of the composition comprising carbon monoxide, carbon dioxide, methane, hydrogen, acetylene, ethylene, and heavier hydrocarbons as the acetylene fed to the catalytic distillation reactor system.

5. The process of claim 1, wherein the light solvent comprises at least one of butane, isobutane, isopentane, pentane, and dimethyl ether.

6. The process of claim 1, further comprising:
   feeding at least a portion of the vapor fraction to a separation unit to recover a fraction having an enriched ethylene concentration.

7. A process for the production of ethylene, the process comprising:
   feeding hydrogen, a heavy solvent, a light solvent, and acetylene to a down-flow reactor comprising at least one reaction zone comprising a hydrogenation catalyst;
   concurrently in the down-flow reactor:
      contacting acetylene and hydrogen in the presence of the hydrogenation catalyst to convert at least a portion of the acetylene to ethylene;
      boiling at least a portion of the light solvent from a liquid phase to a vapor phase;
   recovering a reactor effluent comprising heavy solvent, light solvent, and ethylene;
   condensing at least a portion of the light solvent in the vapor phase;
   recovering a solvent fraction comprising the heavy solvent and the light solvent;
   recovering a product fraction comprising ethylene,
   wherein the heavy solvent comprises at least one of cyclohexane, propionitrile, methylcyclohexane, furfural, ethylamine, cyclic organic carbonate esters, and dimethylacetamide.

8. The process of claim 7, wherein the down-flow reactor is operated under pulse flow conditions.

9. The process of claim 7, further comprising recycling at least a portion of the solvent fraction to the top of the down-flow reactor to maintain the catalyst as fully wetted.

10. The process of claim 7, wherein the product fraction further comprises at least one of hydrogen, methane, carbon dioxide, and carbon monoxide, the process further comprising:
    feeding at least a portion of the vapor fraction to a separation unit to recover a fraction having an enriched ethylene concentration.

11. A process for converting methane to ethylene, the process comprising:
    heating methane to a temperature of at least 1200° C. to form a pyrolysis composition comprising acetylene, ethylene, hydrogen, carbon monoxide, carbon dioxide, and methane;
    feeding a heavy solvent, a light solvent, and the pyrolysis composition to a catalytic distillation reactor system comprising at least one reaction zone comprising a hydrogenation catalyst;
    concurrently in the catalytic distillation reactor system:
       contacting acetylenes and hydrogen in the presence of the hydrogenation catalyst to convert at least a portion of the acetylenes to ethylene;
       fractionating the feed components to form a light fraction, comprising the light solvent, ethylene and components lighter than ethylene, and a heavy fraction, comprising the heavy solvent;
    recovering the light fraction from the catalytic distillation reactor system as a first overheads fraction;
    recovering the heavy fraction from the catalytic distillation reactor system as a first bottoms fraction;
    condensing at least a portion of the first overheads fraction to form a vapor fraction, comprising ethylene and components lighter than ethylene, and a liquid fraction, comprising the light solvent;
    returning at least a portion of the liquid fraction to the catalytic distillation reactor system as a reflux; and
    returning at least a portion of the heavy fraction to the catalytic distillation reactor system at a location above the at least one reaction zone,
    wherein the heavy solvent comprises at least one of cyclohexane, propionitrile, methylcyclohexane, furfural, ethylamine, dimethylformamide, cyclic organic carbonate esters, and dimethylacetamide.

12. The process of claim 11, wherein the pyrolysis composition is fed to the catalytic distillation reactor system at a location below the at least one reaction zone.

13. The process of claim 11, further comprising returning at least a portion of the liquid fraction to the catalytic distillation reactor system at a location below the at least one reaction zone.

14. The process of claim 11, wherein the light solvent comprises at least one of butane, isobutane, isopentane, pentane, and dimethyl ether.

15. The process of claim 11, further comprising:
feeding at least a portion of the vapor fraction to a separation unit to recover a fraction having an enriched ethylene concentration.

16. The process of claim 11, wherein the heating is in the presence of a pyrolysis catalyst.

17. The process of claim 11, wherein the at least one reaction zone is at a temperature within the range from about 15° C. to about 205° C. (about 60° F. to about 400° F.).

18. The process of claim 11, wherein the at least one reaction zone is at a temperature within the range from about 20° C. to about 150° C. (about 70° F. to about 300° F.).

19. The process of claim 11, wherein the at least one reaction zone is at a pressure within the range from about 2.7 bar to about 16 bar (about 25 psig to about 220 psig).

20. The process of claim 11, wherein the at least one reaction zone is at a pressure within the range from about 4.5 bar to about 13.4 bar (about 50 psig to about 180 psig).

\* \* \* \* \*